United States Patent
Birner et al.

(10) Patent No.: US 7,923,452 B2
(45) Date of Patent: Apr. 12, 2011

(54) FUNGICIDAL MIXTURES COMPRISING BOSCALID AND PYRIMETHANIL

(75) Inventors: Erich Birner, Altleiningen (DE); Richard Milling, Manchester (GB); Randall Evan Gold, Obrigheim (DE); Reinhard Stierl, Kaohsiung County (TW)

(73) Assignee: BASF SE, Ludwigshafen (DE)

( * ) Notice: Subject to any disclaimer, the term of this patent is extended or adjusted under 35 U.S.C. 154(b) by 345 days.

(21) Appl. No.: 12/092,053

(22) PCT Filed: Nov. 6, 2006

(86) PCT No.: PCT/EP2006/068105
§ 371 (c)(1), (2), (4) Date: Apr. 29, 2008

(87) PCT Pub. No.: WO2007/054473
PCT Pub. Date: May 18, 2007

(65) Prior Publication Data
US 2008/0293567 A1    Nov. 27, 2008

(30) Foreign Application Priority Data
Nov. 10, 2005   (EP) .................................. 05024522

(51) Int. Cl.
*A01N 43/40*   (2006.01)
*A01N 43/54*   (2006.01)

(52) U.S. Cl. ................... 514/275; 514/355; 504/100

(58) Field of Classification Search ................. 514/275, 514/355
See application file for complete search history.

(56) References Cited

U.S. PATENT DOCUMENTS

| | | |
|---|---|---|
| 5,330,995 A | 7/1994 | Eicken et al. |
| 7,087,239 B2 | 8/2006 | Bratz et al. |
| 2006/0154825 A1 | 7/2006 | Mayer et al. |
| 2009/0069356 A1 * | 3/2009 | Bylemans et al. ............ 514/275 |

FOREIGN PATENT DOCUMENTS

| | | |
|---|---|---|
| DE | 151 404 A1 | 10/1981 |
| EP | 0 545 099 A2 | 6/1993 |
| WO | WO-03/029219 A1 | 4/2003 |
| WO | WO-2004/072039 A1 | 8/2004 |

* cited by examiner

*Primary Examiner* — John Pak
(74) *Attorney, Agent, or Firm* — Birch, Stewart, Kolasch & Birch, LLP

(57) ABSTRACT

Fungicidal mixtures comprising
(1) boscalid of the formula (I)

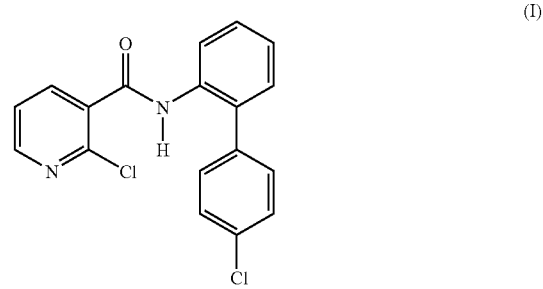

(I)

and
(2) pyrimethanil of the formula (II)

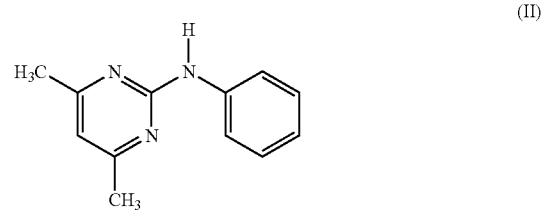

(II)

in a synergistically effective amount, methods for controlling harmful fungi using mixtures of boscalid (I) and pyrimethanil (II) and the use of boscalid (I) and pyrimethanil (II) for preparing such mixtures, compositions comprising these mixtures and also seed comprising these mixtures.

8 Claims, No Drawings

FUNGICIDAL MIXTURES COMPRISING BOSCALID AND PYRIMETHANIL

The present invention relates to fungicidal mixtures comprising
(1) boscalid of the formula (I)

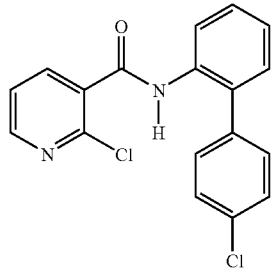

and
(2) pyrimethanil of the formula (II)

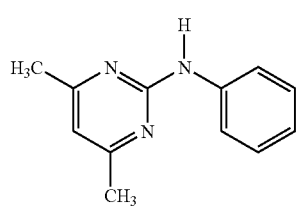

in a synergistically effective amount.

Moreover, the invention relates to a method for controlling harmful fungi using mixtures of boscalid (I) and pyrimethanil (II), to the use of boscalid (I) and pyrimethanil (II) for preparing such mixtures, to fungicidal compositions comprising these mixtures and also to seed comprising these mixtures Boscalid is known from EP-A 545099.

Pyrimethanil is known from DD-A 151404.

With a view to reducing the application rates and improving the activity spectrum of the known compounds (I) and (II), it was an object of the present invention to provide mixtures having an improved activity against harmful fungi at a reduced total amount of active compounds applied (synergistic mixtures).

Accordingly, we have found the mixture, defined at the outset, of boscalid and pyrimethanil. Moreover, we have found that simultaneous, that is joint or separate, application of boscalid (I) and pyrimethanil (II) or successive application of boscalid (I) and pyrimethanil (II) allows better control of harmful fungi than application of the individual compounds alone.

Boscalid may be present in different crystal modifications and in hydrated form (cf. WO 03/29219 and WO 2004/72039); formula I comprises all modifications and hydrates.

The mixtures of the compound (I) with the active compound (II), or the simultaneous, that is joint or separate, use of the compound (I) with active compound (II), are/is distinguished by excellent activity against a broad spectrum of phytopathogenic fungi, in particular from the classes of the Ascomycetes, Basidiomycetes, Deuteromycetes and Peronosporomycetes (syn. Oomycetes). Some of them are systemically active and can be used in crop protection as foliar fungicides, as fungicides for seed dressing and as soil fungicides.

They are particularly important for controlling a multitude of fungi on various cultivated plants, such as bananas, cotton, vegetable species (for example cucumbers, beans, tomatoes and cucurbits), barley, grass, oats, coffee, potatoes, corn, fruit species, rice, rye, soybeans, grapevines, wheat, ornamental plants, sugar cane and also on a large number of seeds.

They are especially suitable for controlling the following plant diseases:
*Alternaria* species on vegetables, rapeseed, sugar beet and fruit and rice,
*Aphanomyces* species on sugar beet and vegetables,
*Bipolaris* and *Drechslera* species on corn, cereals, rice and lawns,
*Blumeria graminis* (powdery mildew) on cereals,
*Botrytis cinerea* (gray mold) on strawberries, vegetables, flowers and grapevines,
*Bremia lactucae* on lettuce,
*Cercospora* species on corn, soybeans, rice and sugar beet,
*Cochliobolus* species on corn, cereals, rice (e.g., *Cochiobolus sativus* on cereals, *Cochliobolus miyabeanus* on rice),
*Colletotricum* species on soybeans and cotton,
*Drechslera* species on cereals and corn,
*Exserohilum* species on corn,
*Erysiphe cichoracearum* and *Sphaerotheca fuliginea* on cucurbits,
*Fusarium* and *Verticillium* species on various plants,
*Gaeumanomyces graminis* on cereals,
*Gibberella* species on cereals and rice (e.g., *Gibberella fujikuroi* rice),
Grain staining complex on rice,
*Helminthosporium* species on corn and rice,
*Michrodochium nivale* on cereals,
*Mycosphaerella* species on cereals, bananas and peanuts,
*Phakopsara pachyrhizi* and *Phakopsara meibomiae* on soybeans,
*Phomopsis* species on soybeans and sunflowers,
*Phytophthora infestans* on potatoes and tomatoes,
*Plasmopara viticola* on grapevines,
*Podosphaera leucotricha* on apples,
*Pseudocercosporella herpotrichoides* on cereals,
*Pseudoperonospora* species on hops and cucurbits,
*Puccinia* species on cereals and corn,
*Pyrenophora* species on cereals,
*Pyricularia oryzae, Corticium sasakii Sarocladium oryzse, S. attenuatum, Entyloma oryzae* on rice,
*Pyricularia grisea* on lawns and cereals,
*Pythium* spp. on lawns, rice, corn, cotton, rapeseed, sunflowers, sugar beet, vegetables and other plants,
*Rhizoctonia* species on cotton, rice, potatoes, lawns, corn, rapeseed, potatoes, sugar beet, vegetables and other plants,
*Sclerotinia* species on rapeseed and sunflowers,
*Septoria tritci* and *Stagonospora nodorum* on wheat,
*Elysiphe* (syn. *Uncinula*) *necator* on grapevines,
*Setospaeria* species on corn and lawns,
*Sphacelotheca reilinia* on corn,
*Thievaliopsis* species on soybeans and cotton,
*Tilletia* species on cereals,
*Ustilago* species on cereals, corn and sugar beet, and
*Venturia* species (scab) on apples and pears.

Moreover, the mixtures according to the invention are suitable for controlling harmful fungi such as *Paecilomyces variotii* the protection of materials (for example wood, paper, paint dispersions, fibers or fabrics) and in the protection of stored products.

Boscalid (i) and pyrimethanil (II) can be applied simultaneously, that is jointly or separately, or in succession, the sequence, in the case of separate application, generally not having any effect on the result of the control measures.

When providing the mixtures, it is preferred to employ the pure active compounds (I) and (II), to which further active compounds against harmful fungi or against other pests, such as insects, arachnids or nematodes, or else herbicidal or growth-regulating active compounds or fertilizers can be added.

What is applied are usually mixtures of boscalid (I) and pyrimethanil (II). However, in certain cases it may be advantageous to use mixtures of boscalid (I) with two or, if appropriate, more active components.

The compound (I) and the active compound (II) are usually applied in a weight ratio of from 100:1 to 1:100, preferably from 20:1 to 1:20, in particular from 10:1 to 1:10.

The further active components are, if desired, mixed in a ratio of from 20:1 to 1:20 to the compound (I).

Depending on the type of compound and the desired effect, the application rates of the mixtures according to the invention are, especially in the case of agricultural crop areas, from 5 g/ha to 2000 g/ha, preferably from 20 to 900 g/ha, in particular from 50 to 750 g/ha.

Correspondingly, the application rates for boscalid (I) are generally from 1 to 1000 g/ha, preferably from 10 to 900 g/ha, in particular from 20 to 750 g/ha. Correspondingly, the application rates for pyrimethanil (II) are generally from 1 to 2000 g/ha, preferably from 10 to 900 g/ha, in particular from 40 to 750 g/ha.

In the treatment of seed, application rates of mixture are generally from 1 to 1000 g per 100 kg of seed, preferably from 1 to 750 g per 100 kg, in particular from 5 to 500 g per 100 kg.

The method for controlling harmful fungi is carried out by the separate or joint application of boscalid (I) and pyrimethanil (II) or a mixture of boscalid I and pyrimethanil II by spraying or dusting the seeds, the plants or the soil before or after sowing of the plants or before or after emergence of the plants.

The mixtures according to the invention or boscalid (I) and pyrimethanil (II) can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries suitable for this purpose are essentially:
water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used,
carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations: 1. Products for dilution with water

A) Water-Soluable Concentrates (SL)

10 parts by weight of (I), (II) or a mixture of (I) and (II) are dissolved in 90 parts by weight of water or of a water-soluble solvent. As an alternative, wetting agents or other auxiliaries are added. The active compound dissolves upon dilution with water. This gives a formulation having an active compound content of 10% by weight.

B) Dispersible Concentrates (DC)

20 parts by weight of (I), (II) or a mixture of (I) and (II) are dissolved in 70 parts by weight of cyclohexanone with addition of 10 parts by weight of a dispersant, for example polyvinylpyrrolidone. Dilution with water gives a dispersion. The active compound content is 20% by weight.

C) Emulsifiable Concentrates (EC)

15 parts by weight of (I), (II) or a mixture of (II) and (II) are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D) Emulsions (EW, EO)

25 parts by weight of (I), (II) or a mixture of (I) and (II) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion. The formulation has an active compound content of 25% by weight.

E) Suspensions (SC, OD)

In an agitated bali mill, 20 parts by weight of (i), (ii) or a mixture of (I) and (II) are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F) Water-Dispersible Granules and Water-Soluable Granules (WG, SG)

50 parts by weight of (I), (II) or a mixture of (I) and (II) are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G) Water-Dispersible Powders and Water-Soluable Powders (WP, SP)

75 parts by weight of (I), (II) or a mixture of (I) and (II) are ground in a rotor-stator mill with addition of 25 parts by weight of dispersants, wetting agents and silica gel. Dilution with water gives a stable dispersion or solution of the active compound. The active compound content of the formulation is 75% by weight.

2. Products to be Applied Undiluted

H) Dustable Powders (DP)

5 parts by weight of (I), (II) or a mixture of (I) and (II) are ground finely and mixed intimately with 95 parts by weight of finely divided kaolin. This gives a dustable product having an active compound content of 5% by weight.

J) Granules (GR, FG, GG, MG)

0.5 part by weight of (I), (II) or a mixture of (I) and (II) is ground finely and associated with 99.5 parts by weight of carriers. Current methods are extrusion, spray-drying or the fluidized bed. This gives granules to be applied undiluted having an active compound content of 0.5% by weight.

K) ULV Solutions (UL)

10 parts by weight of (I), (II) or a mixture of (I) and (II) are dissolved in 90 parts by weight of an organic solvent, for example xylene. This gives a product to be applied undiluted having an active compound content of 10% by weight.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible thereby to apply formulations comprising over 95% by weight of active compound, or even to apply the active compound without additives.

Oils of various types, wetters, adjuvants, may be added to the active compounds, even, if appropriate, not until immediately prior to use (tank mix). These agents are typically admixed with the compositions according to the invention in a weight ratio of from 1:100 to 100:1, preferably from 1:10 to 10:1.

The compounds I and II or the mixtures or the corresponding formulations are applied by treating the harmful fungi, the plants, seeds, soils, areas, materials or spaces to be kept free from them with a fungicidally effective amount of the mixture or, in the case of separate application, of the compounds I and II. Application can be carried out before or after infection by the harmful fungi.

The fungicidal activity of the individual compounds and the mixtures according to the invention was demonstrated by the following tests.

The active compounds, separately or jointly, were prepared as a stock solution comprising 25 mg of active compound which was made up to 10 ml using a mixture of acetone and/or dimethyl sulfoxide and the emulsifier Uniperol® EL (wetting agent having an emulsifying and dispersing action based on ethoxylated alkylphenols) in a ratio by volume of solvent/emulsifier of 99:1. The mixture was then made up to 100 ml with water. This stock solution was diluted with the solvent/emulsifier/water mixture described to give the concentration of active compound stated below.

The visually determined percentages of infected leaf areas were converted into efficacies in % of the untreated control:

The efficacy (E) is calculated as follows using Abbot's formula.

$$W = (1 - \alpha/\beta) \cdot 100$$

$\alpha$ corresponds to the fungicidal infection of the treated plants in % and $\beta$ corresponds to the fungicidal infection of the untreated (control) plants in %

At an efficacy of 0, the infection level of the treated plants corresponds to that of the untreated control plants; at an efficacy of 100, the treated plants are not infected.

The expected efficacies of active compound mixtures were determined using Colby's formula (S. R. Colby, "Calculating synergistic and antagonistic responses of herbicide combinations", Weeds 15, 20-22 (1967)) and compared with the observed efficacies.

Colby's formula:

$$E = x + y - x \cdot y/100$$

E expected efficacy, expressed in % of the untreated control, when using the mixture of the active compounds A and B at the concentrations a and b;

x efficacy, expressed in % of the untreated control, when using the active compound A at the concentration a;

y efficacy, expressed in % of the untreated control, when using the active compound B at the concentration b;

USE EXAMPLE 1

Protective Activity Against *Puccinia recondita* on Wheat (Brown Rust of Wheat) (Puccrt P1)

Leaves of potted wheat seedlings of the cultivar "Kanzler" were sprayed to runoff point with an aqueous suspension having the concentration of active compound stated below. The next day the treated plants were inoculated with a spore suspension of brown rust of wheat (*Puccinia recondita*). The plants were then placed in a chamber at high atmospheric humidity (90 to 95%) at 20 to 22° C. for 24 hours. During this time, the spores germinated and the germ tubes penetrated into the leaf tissue. The next day, the test plants were returned to the greenhouse and cultivated at temperatures between 20 and 22° C. and 65 to 70% relative atmospheric humidity for a further 7 days. The extent of the rust fungus development on the leaves was then determined visually.

| Active compound/Active compound combination | Conc (ppm) | Ratio | Observed activity (%) | Activity calculated according to Colby (%) | Synergism | Level of synergism (%) |
|---|---|---|---|---|---|---|
| Pyrimethanil | 2 | | 0 | | | |
| | 4 | | 0 | | | |
| Boscalid | 8 | | 22 | | | |
| Boscalid | 8 | 4:1 | 56 | 22 | Yes | 34 |
| Pyrimethanil | 2 | | | | | |
| Boscalid | 8 | 2:1 | 67 | 22 | Yes | 45 |
| Pyrimethanil | 4 | | | | | |
| Untreated | | | 90% infection | | | |

The invention claimed is:

1. A fungicidal mixture comprising
(1) boscalid of the formula (I)

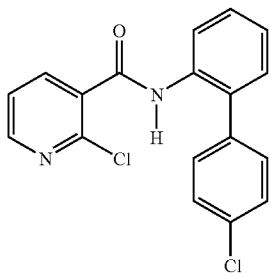

(I)

and
(2) pyrimethanil of the formula (II)

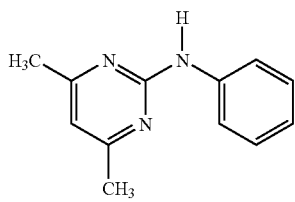

(II)

in a synergistically effective amount.

2. The fungicidal mixture according to claim 1 wherein the weight ratio of boscalid (I) to pyrimethanil (II) is from 100:1 to 1:100.

3. A method for controlling phytopathogenic harmful fungi wherein the harmful fungi, their habitat or the plants, the soil or seed to be protected against fungal attack are treated with an effective amount of a mixture according to claim 1.

4. The method according to claim 3 wherein the fungicidal mixture is applied in an amount of from 5 g/ha to 2000 g/ha.

5. The method according to claim 3 wherein the fungicidal mixture is applied in an amount of from 1 g to 1000 g per 100 kg of seed.

6. Seed comprising the mixture according to claim 1 in an amount of from 1 g to 1000 g per 100 kg of seed.

7. A method for preparing a composition suitable for controlling harmful fungi which comprises forming the fungicidal mixture according to claim 1.

8. A fungicidal composition comprising the fungicidal mixture according to claim 1 and a solid or liquid carrier.

* * * * *